[19] United States Patent
Boger et al.

[11] 3,968,223
[45] July 6, 1976

[54] CONTROL OF INSECTS AND ACARIDS WITH O-(2-VINYLPHENYL)-THIOLPHOSPHATES

[75] Inventors: Manfred Böger, Haltingen, Germany; Jozef Drabek, Allschwil, Switzerland

[73] Assignee: Ciba-Geigy Corporation, Ardsley, N.Y.

[22] Filed: May 27, 1975

[21] Appl. No.: 581,069

Related U.S. Application Data

[62] Division of Ser. No. 449,416, March 8, 1974, Pat. No. 3,898,306.

[30] Foreign Application Priority Data

Mar. 15, 1973  Switzerland.......................... 3776/73
Jan. 30, 1974  Switzerland.......................... 1261/74

[52] U.S. Cl. ................................................. 424/219
[51] Int. Cl.² ............................................. A01N 9/36
[58] Field of Search .................................... 424/219

[56] References Cited
UNITED STATES PATENTS 2,275,041   3/1942   Britton et al...................... 260/956

*Primary Examiner*—Albert T. Meyers
*Assistant Examiner*—Allen J. Robinson
*Attorney, Agent, or Firm*—Frederick H. Rabin

[57] ABSTRACT

Compounds of the formula

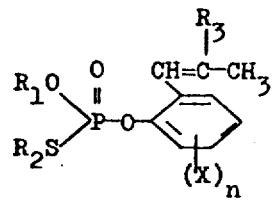

wherein $R_1$ represents methyl or ethyl, $R_2$ represents n-propyl, isopropyl, isobutyl, sec. butyl or n-amyl, $R_3$ represents hydrogen or methyl, X represents hydrogen, halogen, methyl, methylthio, methylsulphinyl, methoxy or acetyl, and $n$ is 1 to 3, and their use for controlling insects, representatives of the order Acarina, phytopathogenic fungi and phytopathogenic nematodes are disclosed.

10 Claims, No Drawings

CONTROL OF INSECTS AND ACARIDS WITH O-(2-VINYLPHENYL)-THIOLPHOSPHATES

This is a division of application Ser. No. 449,416 filed on Mar. 8, 1974, now U.S. Pat. No. 3,898,306.

The present invention provides thiolphosphoric acid esters, a process for their manufacture, and a method of using them in pest control.

The thiolphosphoric acid esters have the formula

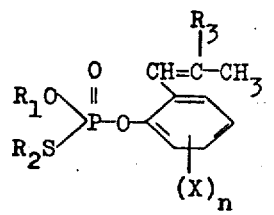

(I)

wherein $R_1$ represents methyl or ethyl, $R_2$ represents n-propyl, isopropyl, isobutyl, sec. butyl or n-amyl, $R_3$ represents hydrogen or methyl, X represents hydrogen, halogen, methyl, methylthio, methylsulphinyl, methoxy, or acetyl, and n is 1 to 3.

The term "halogen" is to be understood as meaning fluorine, chlorine, and/or bromine.

Preferred compounds on account of their action are those of the formula I wherein $R_1$ represents ethyl, $R_2$ represents n-propyl, $R_3$ represents hydrogen or methyl, X represents hydrogen, chlorine, methyl, methylthio, or methylsulphinyl, and n is 1, 2, or 3.

The compounds of the formula I can be manufactured by methods that are known per se:

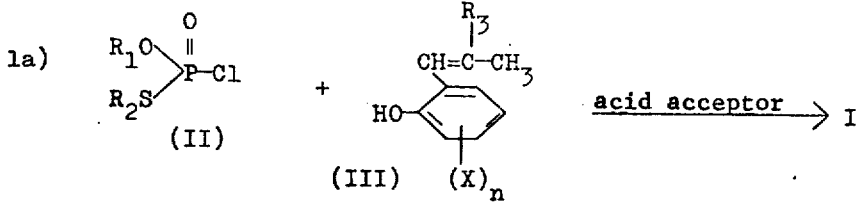

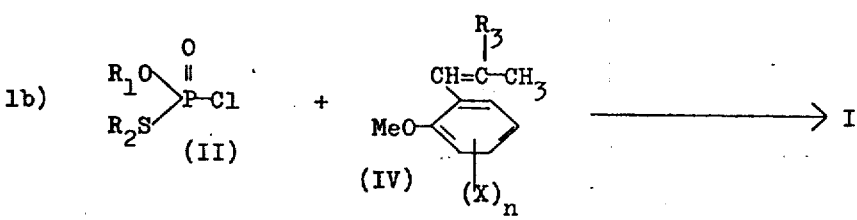

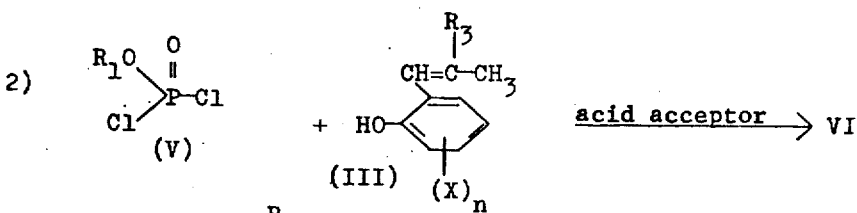

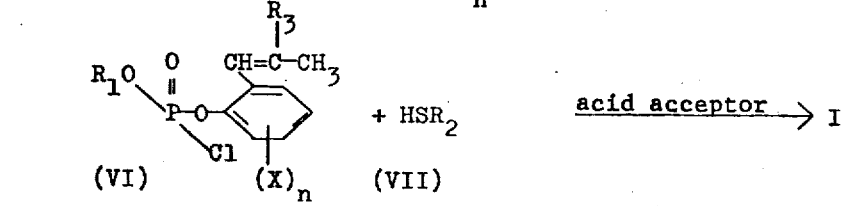

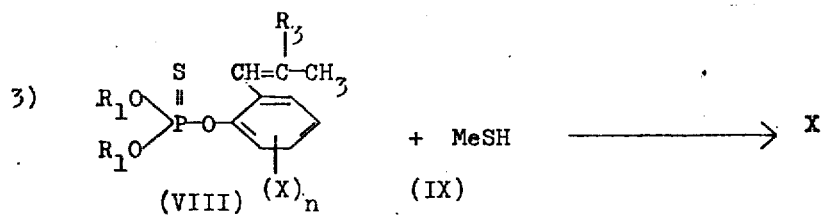

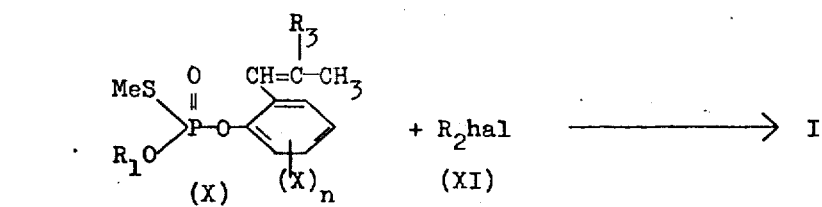

In the formulae II to XI, the symbols $R_1$, $R_2$, $R_3$, X and n have the meanings as given for the formula I and Me represents an alkali metal, in particular sodium or potassium, ammonium or alkylammonium, and "hal" represents a halogen atom, such as fluorine, chlorine, bromine, or iodine.

Suitable acid acceptors are tertiary amines, e.g. trialkylamines, pyridine, dialkyl anilines; inorganic bases, e.g. hydrides, hydroxides, carbonates and bicarbonates of alkali metals and alkaline earth metals.

During the reactions it is sometimes necessary to use catalysts, e.g. copper or copper chloride. Processes 1a and 1b, 2 and 3 are carried out at a reaction temperature between 0° and 130°C, at normal pressure, and in solvents or diluents.

Examples of suitable solvents or diluents are: ethers and ethereal compounds, e.g. diethyl ether, dipropyl ether, dioxan, tetrahydrofuran; amides, e.g. N,N-dialkylated carboxy amides; aliphatic, aromatic and halogenated hydrocarbons, in particular benzene, toluene, xylenes, chloroform, chlorobenzene; nitriles, e.g. acetronitriles; dimethyl sulphoxide; ketones, e.g. acetone, methyl ethyl ketone; water. Ethanol is also suitable for process 3.

The starting materials of the formulae II, V, and VIII can be manufactured in analogous manner to known methods, e.g. those described in "Organic Reactions II", pages 1 to 48.

The compounds of the formula I have a broad biocidal activity and can be used for controlling a variety of plant and animal pests. Surprisingly, however, they act better against e.g. larvae of Spodoptera littoralis than analogous compounds of German Offenlegungsschrift 2.163.391.

In addition, however, they are also suitable for controlling all development stages, e.g. eggs, larvae, pupae, nymphs, and adults of insects of the families:
Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Paralidae, Galleriidae, Culicidae, Tipulidae, Stomoxydae, Muscidae, Calliphoridae, Trypetidae, Pulicidae, as well as Acaridae of the families: Ixodidae, Argasidae, Tetranychidae, Dermanyssidae.

By addition of other insecticides and/or acaricides it is possible to improve substantially the insecticidal or acaricidal action and do adapt it to given circumstances.

Examples of suitable additives are: organic phosphorus compounds, nitrophenols and derivatives thereof; pyrethrines; formamidines; ureas; carbamates and chlorinated hydrocarbons.

In addition to the above mentioned properties, the compounds of the formula I are also active against fungi, especially against the phytopathogenic fungi belonging to the class of Basidomycetes, e.g. *Piricularia oryzae*. The compounds of the formula I are also suitable for controlling phypathogenic nematodes.

The compounds of the formula I may be used as pure active substance or together with suitable carriers and/or additives. Suitable carriers and additives can be solid or liquid and correspond to the substances conventionally used in formulaion technology, for example natural or regenerated substances, solvents, dispersants, wetting agents, adhesives, thickeners, binders and/or fertilisers.

For application, the compounds of the formula I may be processed to dusts, emulsion concentrates, granules, dispersions, sprays, to solutions or suspensions, in the conventional formulation which is commonly employed in application technology. Mention is also to be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances can take, and be used in, the following forms:

Solid forms:
dusts, tracking agents, granules, coated granules, impregnated granules and homogeneous granules.
Liquid forms:
a. active substances which are dispersible in water: wettable powders, pasts, emulsions:
b. solutions.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:
a.
5 parts of active substance
95 parts of talcum
b.
2 parts of active substance
1 part of highly disperse silicic acid
97 parts of talcum.
The active substances are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3–0.8 mm).
The active substance is mixed with epichlorohydrin and dissolved with 6 parts of acetone; the polyethylene glycol and cetyl polyglycol ether are then added. The resulting solution is sprayed on kaolin, and the acetone is subsequently evaporated in vacuo.

Wettable powder

The following constituents are used for the preparation of (a) a 40%, (b) and (c) a 25%, and (d) a 10% wettable powder:
a.
40 parts of active substance,
5 parts of sodium lignin sulphonate,
1 part of sodium dibutyl-naphthalene sulphonate,
54 parts of silicic acid.
b.
25 parts of acitve substance, 4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

c.
25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.6 parts of kieselguhr,
46 parts of kaolin.

d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:

a.
10 parts of active substance,
3.4 parts of epoxidised vegetable oil,
13.4 parts of a combination emulsifier consisting of fatty alcohol polyglycol ether and alkylaryl sulphonate calcium salt,
40 parts of dimethylformamide,
43.2 parts of xylene.

b.
25 parts of active substance,
2.5 parts of epoxidised vegetable oil,
10 parts of an alkylarylsulphonate/fatty alcoholglycol ether mixture,
5 parts of dimethylformamide,
57.5 parts of xylene.

From these concentrates it is possible to produce, by dilution with water, emulsions of any desired concentration.

Spray

The following constituents are used to prepared a 5% spray:
5 parts of active substance,
1 part of epichlorohydrin,
94 parts of benzene (boiling limits 160°C-190°C).

EXAMPLE I

O-ethyl-S-n-propyl-O-[2-propenyl-4-methylphenyl]-thiolphosphate 8.08 g of triethylamine are added to a solution of 11.85 g of 2-propenyl-4-methylphenol (b.p. 90°C/0.05 Torr) in 120 ml of benzene. With constant stirring, 16.24 g of 0-ethyl-S-n-propylthiolphosphoric acid chloride are added dropwise at 10°–15°C. Stirring is continued for 12 hours at room temperature. THe triethylamine hydrochloride is filtered off with suction and the filtrate is washed with water, sodium carbonate solution and again with water. The solution is dried over sodium sulphate and the benzene distilled off to yield the compound of the formula

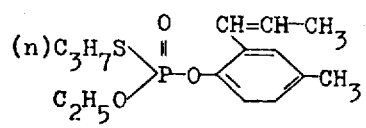

as a yellow oil with a refractive index of $n_D^{20} = 1.5345$. The following compounds are also manufactured in analogous manner:

| Compounds | Physical Data |
|---|---|
| 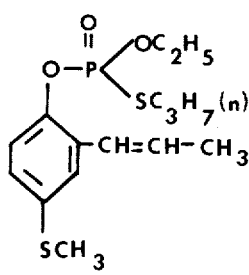 | $n_D^{20} = 1,565$ |
| 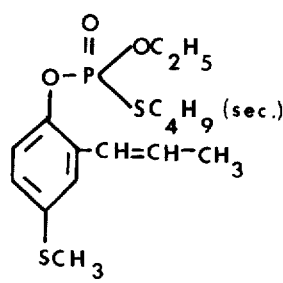 | $n_D^{20} = 1,5654$ |

| Compounds | Physical Data |
|---|---|
| 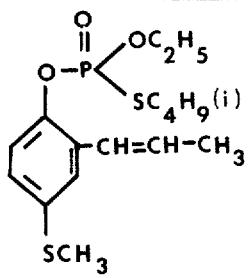 | $n_D^{20} = 1.5552$ |
| 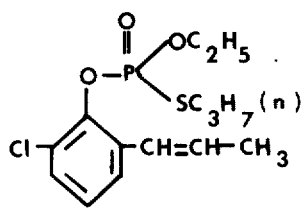 | $n_D^{20} = 1.5478$ |
| 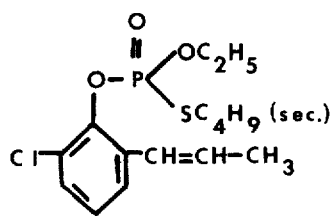 | $n_D^{20} = 1.5379$ |
| 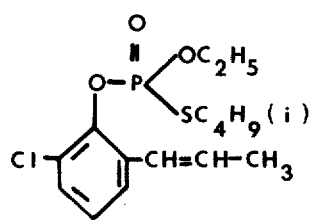 | $n_D^{20} = 1.5423$ |
| 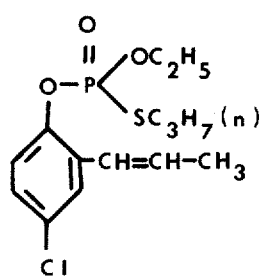 | $n_D^{20} = 1.544$ |
| 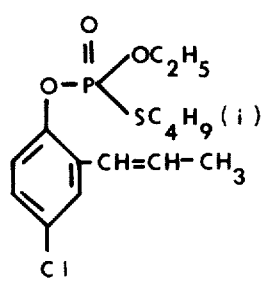 | $n_D^{20} = 1.5409$ |

| Compounds | Physical Data |
|---|---|
| 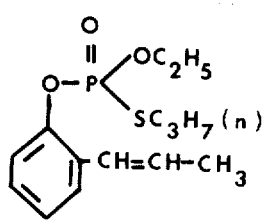 | $n_D^{20} = 1.5375$ |
| 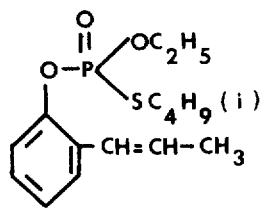 | |
| 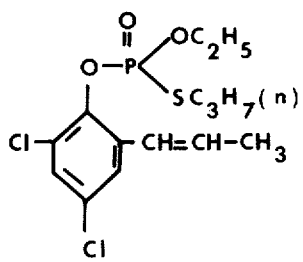 | $n_D^{20} = 1.5568$ |
| 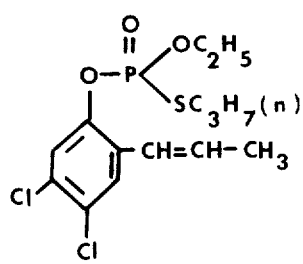 | $n_D^{20} = 1.5538$ |
| 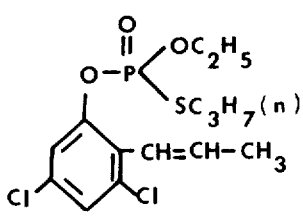 | $n_D^{20} = 1.5518$ |
| 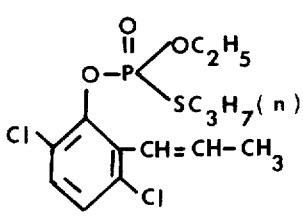 | $n_D^{20} = 1.5532$ |

| Compounds | Physical Data |
|---|---|
| 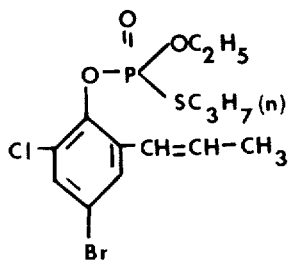 | $n_D^{20} = 1.5692$ |
| 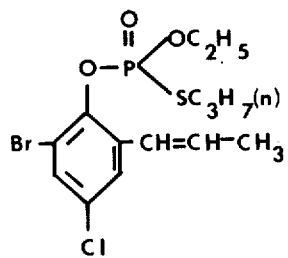 | $n_D^{20} = 1.5692$ |
| 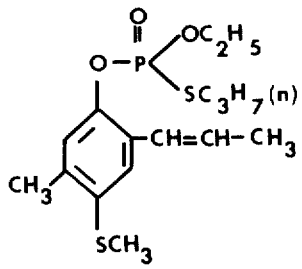 | $n_D^{20} = 1.5668$ |
| 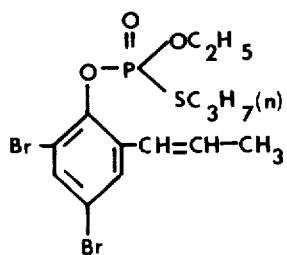 | $n_D^{20} = 1.5801$ |
| 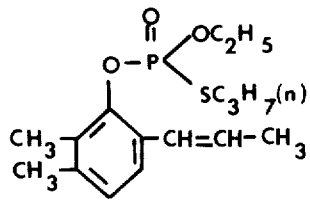 | $n_D^{20} = 1.5410$ |
| 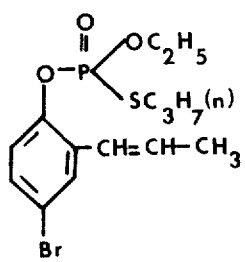 | $n_D^{20} = 1.557$ |

| Compounds | Physical Data |
|---|---|
| 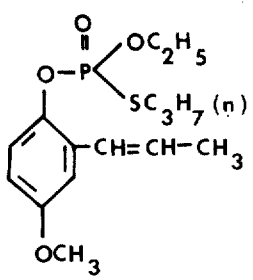 | $n_D^{20} = 1.539$ |
| 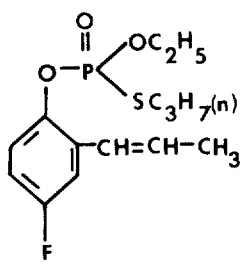 | $n_D^{20} = 1.527$ |
| 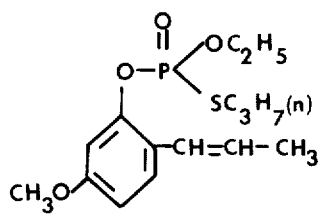 | $n_D^{20} = 1.5435$ |
| 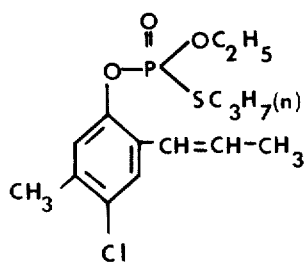 | $n_D^{20} = 1.541$ |
| 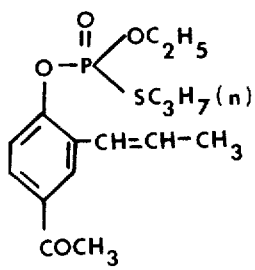 | $n_D^{20} = 1.550$ |
| 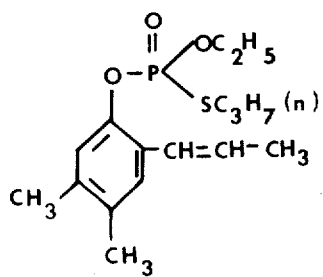 | $n_D^{20} = 1.5335$ |

| Compounds | Physical Data |
|---|---|
| 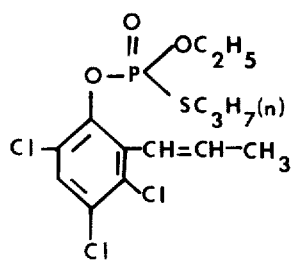 | $n_D^{20} = 1.5614$ |
| 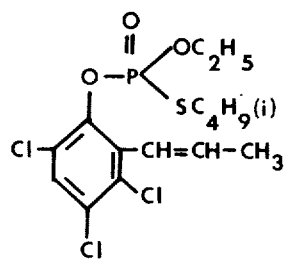 | $n_D^{20} = 1.5539$ |
| 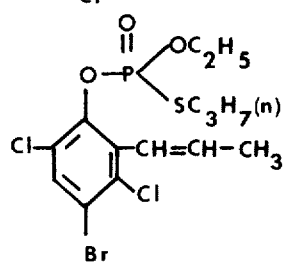 | $n_D^{20} = 1.578$ |
| 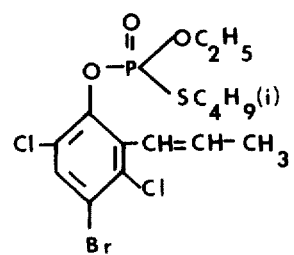 | $n_D^{20} = 1.5614$ |
| 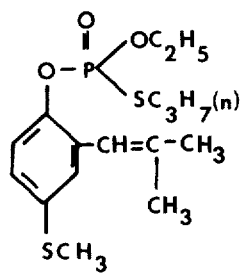 | $n_D^{20} = 1.5598$ |
| 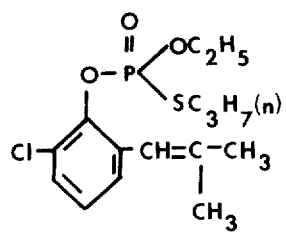 | $n_D^{20} = 1.5389$ |

| Compounds | Physical Data |
|---|---|
| 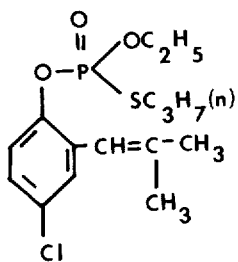 | $n_D^{20} = 1.5368$ |
| 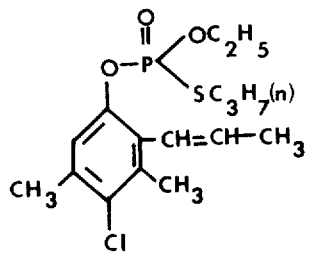 | $n_D^{20} = 1.5405$ |
| 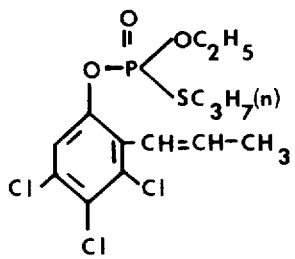 | $n_D^{20} = 1.5618$ |
| 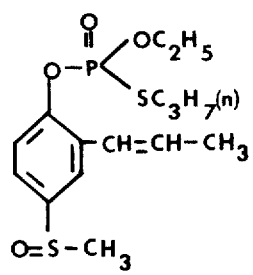 | $n_D^{20} = 1.5619$ |
| 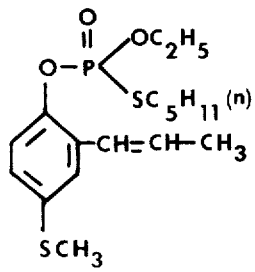 | $n_D^{20} = 1.5614$ |
| 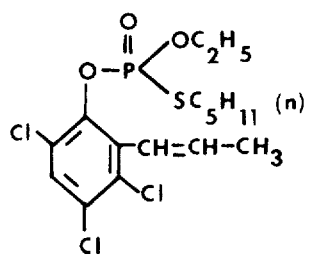 | $n_D^{20} = 1.5581$ |

| Compounds | Physical Data |
|---|---|
| 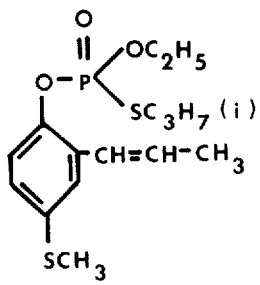 | $n_D^{20} = 1.5639$ |
| 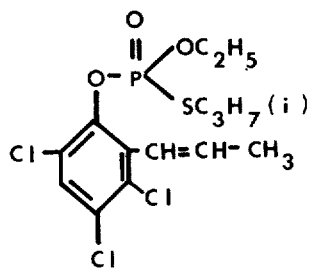 | |
| 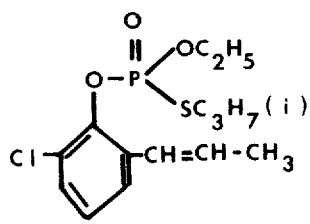 | |

EXAMPLE 2

Insecticidal ingest poison action

Cotton plants were sprayed with a 0.05% aqueous emulsion (obtained from a 10% emulsifiable concentrate). After the coating had dried, the cotton plants were populated with *Spodoptera littoralis* or *Heliothis viresrens* larvae L₃.

The test was carried out at 24°C and 60% relative humidity. In the above test, the compounds according to Example 1 displayed good ingest poison action against *Spodoptera littoralis* and *Heliothis larvae*.

EXAMPLE 3

Action against Chilo suppressalis

Rice seedlings of the variety Caloro were reared in a plastic bowl in such a way that their root system was matted to a disc. This was then immersed in a emulsion of the test preparation in a concentration of 800 ppm and allowed to drip off. Then 5 *Chilo suppressalis* larvae (L₂ larvae) were put into the bowl, followed by the treated plants. The percentage kill of the larvae was determined 5 days later.

In this test, the compound according to Example 1 exhibited good action against *Chilo suppressalis*.

EXAMPLE 4

Action against ticks

A. *Rhipicephalus bursa*

Five adult ticks or 50 tick larvae were counted into a glass tube and immersed for 1 to 2 minutes in 2 ml of an aqueous emulsion from an emulsion series each containing 100, 10, 1 or 0.1 ppm of test substance. The tube was then sealed with a cotton wool plug and placed on its head, so that the active substance emulsion could be absorbed by the cotton wool.

In the case of the adults evaluation took place after 2 weeks, and in that of the larvae after 2 days. Each test was run twice.

B. *Boophilus microplus* (larvae)

Tests were carried out in each case with 20 OP-sensitive larvae using a dilution series analogous to that of test A. (The resistance refers to the tolerability of Diazinon). The compounds according to Example 1 acted in these tests against adults and larvae of *Rhipicephalus bursa* and sensitive and OP-resistant larvae of *Boophilus microplus*.

EXAMPLE 5

Acaricidal action

*Phaseolus vulgaris* (dwarf beans) have an infested piece of leaf from a mass culture of Tetranychus urticae placed on them 12 hours before the test for the acaricidal action. The mobile stages which have migrated are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "interim", the treated plants are kept in greenhouse compartments at 25°C.

The compounds according to Example 1 were active in the above test against eggs, larvae and adults of *Tetranychus urticae*.

EXAMPLE 6

Action against soil nematodes

To test the action against soil nematodes, the active substance in the concentration of 200 ppm is applied to, and intimately mixed with, soil infected with root gall nematodes (*Meloidogyne Arenaria*). Immediately afterwards tomato cuttings are planted in the thus prepared soil in one test run and after a waiting time of 8 days tomato seeds are sown in another test run.

In order to assess the nematocidal action the galls present on the roots are counted 28 days after planting and sowing respectively. In this test, the compounds according to Example 1 display good action against *Meloidogyne arenaria*.

EXAMPLE 7

Action against Piricularia oryzae on Oryzae sativa
Residual protective action

Rice plants were reared for 2 weeks and then sprayed with a spraying broth 0.05% prepared from a wettable powder of the active substance.

After 48 hours the treated plants were infected with a conidial suspension of the fungus. The fungus infection was evaluated after 5 days of incubation at 95–100% relative humidity and 24°C.

In these tests, the active substances according to Example 1 exhibited good action against *Piricularia oryzae*.

We claim:

1. An insecticidal or acaricidal composition comprising (1) as active ingredient, an insecticidally or acaricidally effective amount of a compound of the formula

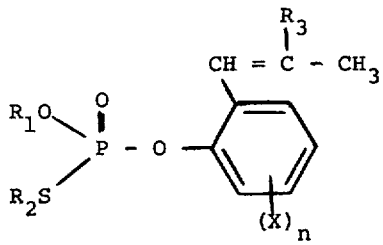

wherein $R_1$ represents methyl or ethyl; $R_2$ represents n-propyl, isopropyl, isobutyl, sec.butyl or n-amyl; $R_3$ represents hydrogen or methyl; X represents hydrogen, halogen or methyl; and $n$ is 1 to 3; and (2) a carrier.

2. A method for combatting insects or acarids which comprises applying thereto an insecticidally or acaricidally effective amount of a compound of the formula

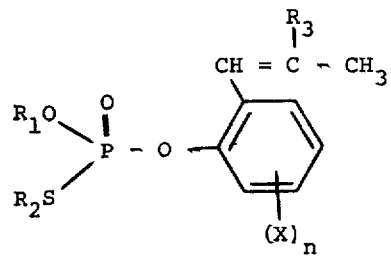

wherein $R_1$ represents methyl or ethyl; $R_2$ represents n-propyl, isopropyl, isobutyl, sec.butyl or n-amyl; $R_3$ repesents hydrogen or methyl; X represents hydrogen, halogen or methyl; and $n$ is 1 to 3.

3. The method according to claim 2 in which $R_1$ represents ethyl; $R_2$ represents n-propyl; and X represents hydrogen, chlorine or methyl.

4. The method according to claim 3 in which the compound is O-ethyl-S-n-propyl-O-[2-(2-methylvinyl)-6-chlorophenyl]-thiolphosphate.

5. The method according to claim 3 in which the compound is O-ethyl-S-n-propyl-O-[2-(2-methylvinyl)-phenyl]-thiolphosphate.

6. The method according to claim 3 in which the compound is O-ethyl-S-n-propyl-O-[2-(2-methylvinyl)-4,6-dichlorophenyl]-thiolphosphate.

7. The method according to claim 3 in which the compound is O-ethyl-S-n-propyl-O-[2-(2-methylvinyl)-3,6-dichlorophenyl]-thiolphosphate.

8. The method according to claim 3 in which the compound is O-ethyl-S-n-propyl-O-[2-(2-methylvinyl)4-chloro-5-methylphenyl]-thiolphosphate.

9. The method according to claim 3 in which the compound is O-ethyl-S-n-propyl-O-[2-(2-methylvinyl)-3,4,6-trichlorophenyl]-thiolphosphate.

10. The method according to claim 3 in which the compound is O-ethyl-S-n-propyl-O-[2-(2-methylvinyl)-4-bromo-3,6-dichlorophenyl]-thiolphosphate.

* * * * *